United States Patent [19]
Baltz et al.

[11] Patent Number: 6,087,143
[45] Date of Patent: Jul. 11, 2000

[54] **GLYCOSYLTRANSFERASE GENE GTFA FROM *AMYCOLATOPSIS ORIENTALIS***

[75] Inventors: Richard H. Baltz; Patricia J. Solenberg, both of Indianapolis, Ind.

[73] Assignee: Eli Lilly and Company, Indianapolis, Ind.

[21] Appl. No.: 09/120,074

[22] Filed: Jul. 21, 1998

Related U.S. Application Data

[62] Division of application No. 08/926,253, Sep. 5, 1997, Pat. No. 5,821,099.
[60] Provisional application No. 60/026,069, Sep. 13, 1996.
[51] Int. Cl.[7] .............................. C12N 9/10; C12N 1/00; C12N 1/14; C12P 19/18
[52] U.S. Cl. .............................. 435/193; 435/97; 435/911
[58] Field of Search .............................. 435/193, 97, 911

[56] References Cited

PUBLICATIONS

S. K. Chung, et al. "Biosynthetic Studies of Aridicin Antibiotics: Microbial Transformations and Glycosylations by Protoplasts." *Journal of Antibiotics* 39(5):652–659 (May 1986).

M. J. Zmijewski, Jr., and B. Briggs. "Biosynthesis of vancomycin: identification of TDP–glucose: aglycosyl–vancomycin glucosyltransferase from *Amycolatopsis orientalis*." *FEMS Microbiology Letters* 5:129–134 (1989).

M. J. Zmijewski, Jr., and J. T. Fayerman. *Genetic and Biochemistry of Antibiotic Production* Ed. L.C. Vining and C. Stuttard. Butterworth Heinemann, Boston. Chapter 18: "Glycopeptide Antibiotics." pp. 71–83 (1995).

*Primary Examiner*—Lisa J. Hobbs
*Attorney, Agent, or Firm*—Raymond S. Parker, III; Thomas D. Webster

[57] ABSTRACT

The invention provides isolated nucleic acid compounds encoding the glycosyltransferase protein GtfA of *Amycolatopsis orientalis*. Also provided are vectors carrying the gtfA gene, transformed heterologous host cells for expressing the GtfA protein, and methods for producing glycopeptide compounds using the cloned gtfA gene.

1 Claim, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1188 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
    (A) NAME/KEY: CDS
    (B) LOCATION: 1..1188

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | CGC | GTG | TTG | ATT | ACG | GGG | TGT | GGA | TCG | CGC | GGA | GAT | ACC | GAA | CCG | 48 |
| Met | Arg | Val | Leu | Ile | Thr | Gly | Cys | Gly | Ser | Arg | Gly | Asp | Thr | Glu | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TTG | GTG | GCA | TTG | GCG | GCA | CGG | TTG | CGG | GAA | CTC | GGT | GCG | GAC | GCG | CGG | 96 |
| Leu | Val | Ala | Leu | Ala | Ala | Arg | Leu | Arg | Glu | Leu | Gly | Ala | Asp | Ala | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| ATG | TGC | CTG | CCG | CCG | GAC | TAC | GTG | GAG | CGG | TGC | GCC | GAG | GTC | GGT | GTG | 144 |
| Met | Cys | Leu | Pro | Pro | Asp | Tyr | Val | Glu | Arg | Cys | Ala | Glu | Val | Gly | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| CCG | ATG | GTG | CCG | GTC | GGT | CGG | GCG | GTG | CGC | GCA | GGG | GCA | CGC | GAG | CCG | 192 |
| Pro | Met | Val | Pro | Val | Gly | Arg | Ala | Val | Arg | Ala | Gly | Ala | Arg | Glu | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| GGA | GAA | CTG | CCG | CCG | GGG | GCG | GCC | GAA | GTC | GTG | ACC | GAG | GTG | GTC | GCC | 240 |
| Gly | Glu | Leu | Pro | Pro | Gly | Ala | Ala | Glu | Val | Val | Thr | Glu | Val | Val | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GAA | TGG | TTC | GAC | AAG | GTC | CCG | GCG | GCC | ATC | GAG | GGG | TGT | GAC | GCG | GTG | 288 |
| Glu | Trp | Phe | Asp | Lys | Val | Pro | Ala | Ala | Ile | Glu | Gly | Cys | Asp | Ala | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| GTG | ACG | ACC | GGC | TTG | CTG | CCC | GCC | GCG | GTC | GCT | GTC | CGG | TCG | ATG | GCC | 336 |
| Val | Thr | Thr | Gly | Leu | Leu | Pro | Ala | Ala | Val | Ala | Val | Arg | Ser | Met | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| GAG | AAG | CTG | GGC | ATC | CCG | TAC | CGC | TAC | ACC | GTG | CTG | TCT | CCG | GAC | CAT | 384 |
| Glu | Lys | Leu | Gly | Ile | Pro | Tyr | Arg | Tyr | Thr | Val | Leu | Ser | Pro | Asp | His | |
| | | 115 | | | | | 120 | | | | | 125 | | | | |

| | | | | | | | | | | | | | | | | |
|---|---|---|---|---|---|---|---|---|---|---|---|---|---|---|---|---|
| CTG | CCG | TCG | GAG | CAA | AGC | CAG | GCG | GAG | CGG | GAC | ATG | TAC | AAC | CAG | GGC | 432 |
| Leu | Pro | Ser | Glu | Gln | Ser | Gln | Ala | Glu | Arg | Asp | Met | Tyr | Asn | Gln | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| GCC | GAC | AGG | CTT | TTC | GGT | GAC | GCG | GTC | AAC | AGC | CAC | CGG | GCC | TCG | ATC | 480 |
| Ala | Asp | Arg | Leu | Phe | Gly | Asp | Ala | Val | Asn | Ser | His | Arg | Ala | Ser | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GGC | CTG | CCA | CCG | GTG | GAG | CAC | CTC | TAC | GAC | TAC | GGC | TAC | ACC | GAT | CAG | 528 |
| Gly | Leu | Pro | Pro | Val | Glu | His | Leu | Tyr | Asp | Tyr | Gly | Tyr | Thr | Asp | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| CCC | TGG | CTG | GCG | GCG | GAC | CCG | GTG | CTG | TCC | CCG | CTG | CGG | CCG | ACG | GAC | 576 |
| Pro | Trp | Leu | Ala | Ala | Asp | Pro | Val | Leu | Ser | Pro | Leu | Arg | Pro | Thr | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| CTC | GGC | ACT | GTG | CAG | ACC | GGT | GCG | TGG | ATC | CTG | CCC | GAC | GAA | CGG | CCG | 624 |
| Leu | Gly | Thr | Val | Gln | Thr | Gly | Ala | Trp | Ile | Leu | Pro | Asp | Glu | Arg | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| CTT | TCC | GCG | GAG | CTG | GAG | GCG | TTT | CTG | GCT | GCC | GGG | TCG | ACG | CCG | GTG | 672 |
| Leu | Ser | Ala | Glu | Leu | Glu | Ala | Phe | Leu | Ala | Ala | Gly | Ser | Thr | Pro | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| TAC | GTG | GGT | TTC | GGC | AGC | TCG | TCC | CGA | CCG | GCA | ACC | GCT | GAC | GCC | GCG | 720 |
| Tyr | Val | Gly | Phe | Gly | Ser | Ser | Ser | Arg | Pro | Ala | Thr | Ala | Asp | Ala | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| AAG | ATG | GCC | ATC | AAG | GCG | GTC | CGT | GCC | AGT | GGC | CGC | CGG | ATC | GTT | CTC | 768 |
| Lys | Met | Ala | Ile | Lys | Ala | Val | Arg | Ala | Ser | Gly | Arg | Arg | Ile | Val | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| TCC | CGC | GGC | TGG | GCC | GAT | TTG | GTC | CTG | CCG | GAC | GAC | GGG | GCC | GAC | TGC | 816 |
| Ser | Arg | Gly | Trp | Ala | Asp | Leu | Val | Leu | Pro | Asp | Asp | Gly | Ala | Asp | Cys | |
| | | | | 260 | | | | | 265 | | | | | 270 | | |

-continued

```
TTC GTG GTC GGC GAA GTG AAC CTT CAG GAG CTG TTC GGC CGG GTG GCC        864
Phe Val Val Gly Glu Val Asn Leu Gln Glu Leu Phe Gly Arg Val Ala
        275                 280                 285

GCC GCC ATC CAC CAC GAC AGC GCG GGC ACG ACG CTG CTG GCC ATG CGG        912
Ala Ala Ile His His Asp Ser Ala Gly Thr Thr Leu Leu Ala Met Arg
290                 295                 300

GCG GGC ATC CCC CAG ATC GTG GTG CGC CGC GTA GTG GAC AAC GTG GTG        960
Ala Gly Ile Pro Gln Ile Val Val Arg Arg Val Val Asp Asn Val Val
305                 310                 315                 320

GAG CAG GCG TAC CAC GCC GAC CGG GTG GCC GAG CTG GGT GTC GGT GTG       1008
Glu Gln Ala Tyr His Ala Asp Arg Val Ala Glu Leu Gly Val Gly Val
                325                 330                 335

GCG GTC GAC GGT CCG GTC CCG ACC ATC GAC TCC TTG TCG GCC GCG CTC       1056
Ala Val Asp Gly Pro Val Pro Thr Ile Asp Ser Leu Ser Ala Ala Leu
        340                 345                 350

GAC ACG GCT CTG GCC CCG GAG ATC CGT GCG CGA GCG ACG ACC GTG GCA       1104
Asp Thr Ala Leu Ala Pro Glu Ile Arg Ala Arg Ala Thr Thr Val Ala
        355                 360                 365

GAC ACG ATT CGC GCC GAT GGG ACA ACG GTG GCC GCG CAG CTG CTG TTC       1152
Asp Thr Ile Arg Ala Asp Gly Thr Thr Val Ala Ala Gln Leu Leu Phe
370                 375                 380

GAC GCG GTC AGC CTG GAA AAG CCG ACT GTT CCC GCC                       1188
Asp Ala Val Ser Leu Glu Lys Pro Thr Val Pro Ala
385                 390                 395
```

(2) INFORMATION FOR SEQ ID NO:2:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Val Leu Ile Thr Gly Cys Gly Ser Arg Gly Asp Thr Glu Pro
1               5                  10                  15

Leu Val Ala Leu Ala Ala Arg Leu Arg Glu Leu Gly Ala Asp Ala Arg
            20                  25                  30

Met Cys Leu Pro Pro Asp Tyr Val Glu Arg Cys Ala Glu Val Gly Val
        35                  40                  45

Pro Met Val Pro Val Gly Arg Ala Val Arg Ala Gly Ala Arg Glu Pro
50                  55                  60

Gly Glu Leu Pro Pro Gly Ala Ala Glu Val Val Thr Glu Val Val Ala
65                  70                  75                  80

Glu Trp Phe Asp Lys Val Pro Ala Ala Ile Glu Gly Cys Asp Ala Val
                85                  90                  95

Val Thr Thr Gly Leu Leu Pro Ala Ala Val Ala Val Arg Ser Met Ala
            100                 105                 110

Glu Lys Leu Gly Ile Pro Tyr Arg Tyr Thr Val Leu Ser Pro Asp His
        115                 120                 125

Leu Pro Ser Glu Gln Ser Gln Ala Glu Arg Asp Met Tyr Asn Gln Gly
    130                 135                 140

Ala Asp Arg Leu Phe Gly Asp Ala Val Asn Ser His Arg Ala Ser Ile
145                 150                 155                 160

Gly Leu Pro Pro Val Glu His Leu Tyr Asp Tyr Gly Tyr Thr Asp Gln
                165                 170                 175

Pro Trp Leu Ala Ala Asp Pro Val Leu Ser Pro Leu Arg Pro Thr Asp
            180                 185                 190
```

```
Leu Gly Thr Val Gln Thr Gly Ala Trp Ile Leu Pro Asp Glu Arg Pro
        195                 200                 205

Leu Ser Ala Glu Leu Glu Ala Phe Leu Ala Ala Gly Ser Thr Pro Val
        210                 215                 220

Tyr Val Gly Phe Gly Ser Ser Arg Pro Ala Thr Ala Asp Ala Ala
225                 230                 235                 240

Lys Met Ala Ile Lys Ala Val Arg Ala Ser Gly Arg Arg Ile Val Leu
                245                 250                 255

Ser Arg Gly Trp Ala Asp Leu Val Leu Pro Asp Asp Gly Ala Asp Cys
            260                 265                 270

Phe Val Val Gly Glu Val Asn Leu Gln Glu Leu Phe Gly Arg Val Ala
        275                 280                 285

Ala Ala Ile His His Asp Ser Ala Gly Thr Thr Leu Leu Ala Met Arg
        290                 295                 300

Ala Gly Ile Pro Gln Ile Val Val Arg Arg Val Val Asp Asn Val Val
305                 310                 315                 320

Glu Gln Ala Tyr His Ala Asp Arg Val Ala Glu Leu Gly Val Gly Val
                325                 330                 335

Ala Val Asp Gly Pro Val Pro Thr Ile Asp Ser Leu Ser Ala Ala Leu
            340                 345                 350

Asp Thr Ala Leu Ala Pro Glu Ile Arg Ala Arg Ala Thr Thr Val Ala
        355                 360                 365

Asp Thr Ile Arg Ala Asp Gly Thr Thr Val Ala Ala Gln Leu Leu Phe
        370                 375                 380

Asp Ala Val Ser Leu Glu Lys Pro Thr Val Pro Ala
385                 390                 395

(2) INFORMATION FOR SEQ ID NO:3:

(i) SEQUENCE CHARACTERISTICS:
        (A) LENGTH: 1188 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

AUGCGCGUGU UGAUUACGGG GUGUGGAUCG CGCGGAGAUA CCGAACCGUU GGUGGCAUUG      60

GCGGCACGGU UGCGGGAACU CGGUGCGGAC GCGCGGAUGU GCCUGCCGCC GGACUACGUG     120

GAGCGGUGCG CCGAGGUCGG UGUGCCGAUG GUGCCGGUCG GUCGGGCGGU GCGCGCAGGG     180

GCACGCGAGC CGGGAGAACU GCCGCCGGGG CGGGCCGAAG UCGUGACCGA GGUGGUCGCC     240

GAAUGGUUCG ACAAGGUCCC GGCGGCCAUC GAGGGGUGUG ACGCGGUGGU GACGACCGGC     300

UUGCUGCCCG CCGCGGUCGC UGUCCGGUCG AUGGCCGAGA AGCUGGGCAU CCCGUACCGC     360

UACACCGUGC UGUCUCCGGA CCAUCUGCCG UCGGAGCAAA GCCAGGCGGA GCGGGACAUG     420

UACAACCAGG GCGCCGACAG GCUUUUCGGU GACGCGGUCA ACAGCCACCG GGCCUCGAUC     480

GGCCUGCCAC CGGUGGAGCA CCUCUACGAC UACGGCUACA CCGAUCAGCC CUGGCUGGCG     540

GCGGACCCGG UGCUGUCCCC GCUGCGGCCG ACGGACCUCG GCACUGUGCA GACCGGUGCG     600

UGGAUCCUGC CCGACGAACG GCCGCUUUCC GCGGAGCUGG AGGCGUUUCU GGCUGCCGGG     660

UCGACGCCGG UGUACGUGGG UUUCGGCAGC UCGUCCCGAC CGGCAACCGC UGACGCCGCG     720
```

-continued

```
AAGAUGGCCA UCAAGGCGGU CCGUGCCAGU GGCCGCCGGA UCGUUCUCUC CCGCGGCUGG      780

GCCGAUUUGG UCCUGCCGGA CGACGGGCC GACUGCUUCG UGGUCGGCGA AGUGAACCUU      840

CAGGAGCUGU UCGGCCGGGU GGCCGCCGCC AUCCACCACG ACAGCGCGGG CACGACGCUG      900

CUGGCCAUGC GGGCGGGCAU CCCCCAGAUC GUGGUGCGCC GCGUAGUGGA CAACGUGGUG      960

GAGCAGGCGU ACCACGCCGA CCGGGUGGCC GAGCUGGGUG UCGGUGUGGC GGUCGACGGU     1020

CCGGUCCCGA CCAUCGACUC CUUGUCGGCC GCGCUCGACA CGGCUCUGGC CCCGGAGAUC     1080

CGUGCGCGAG CGACGACCGU GGCAGACACG AUUCGCGCCG AUGGGACAAC GGUGGCCGCG     1140

CAGCUGCUGU UCGACGCGGU CAGCCUGGAA AAGCCGACUG UUCCCGCC               1188
```

GLYCOSYLTRANSFERASE GENE GTFA FROM *AMYCOLATOPSIS ORIENTALIS*

CROSS-REFERENCE

The present application is a divisional of application Ser. No. 08/926,253, filed Sep. 5, 1997 now U.S. Pat. No. 5,821,099 which claims priority from Provisional application No. 60/026,069, filed Sep. 13, 1996.

BACKGROUND OF THE INVENTION

This invention relates to recombinant DNA technology. In particular the invention pertains to the cloning of glycosyltransferase gene gtfA from *Amycolatopsis orientalis*, the use of the cloned gene to express and purify the encoded enzyme, and a method of using the cloned enzyme for in vitro production of glycopeptide compounds.

The use of antibiotic compounds has had a profound impact on the practice of medicine in the United States and around the world. Two highly effective antibiotic compounds of the glycopeptide class, vancomycin and teichoplanin, have been approved for use in humans.

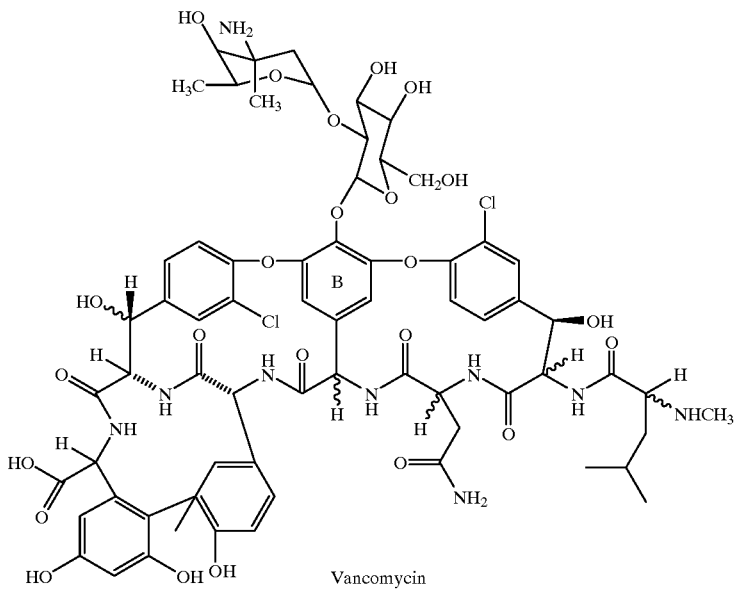

Vancomycin

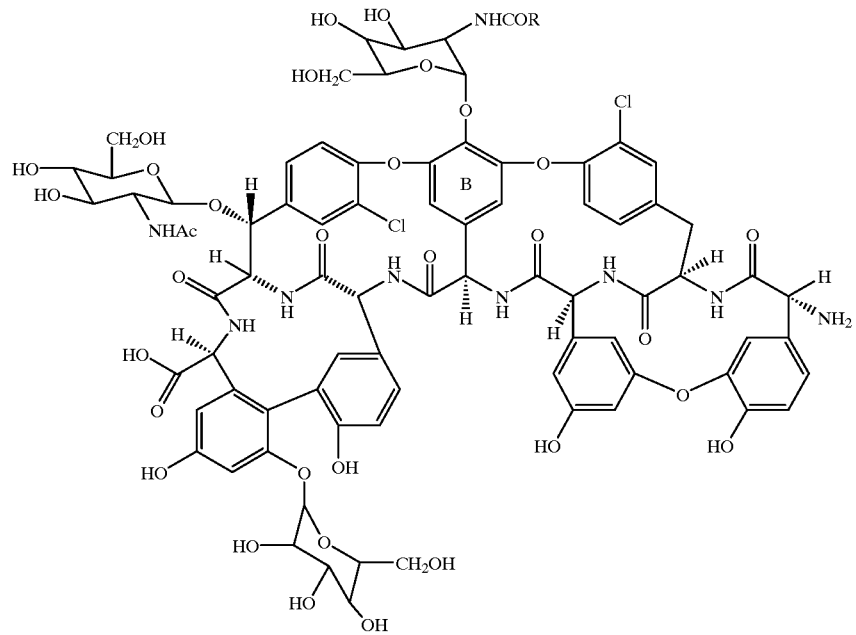

Teicoplanin: R = 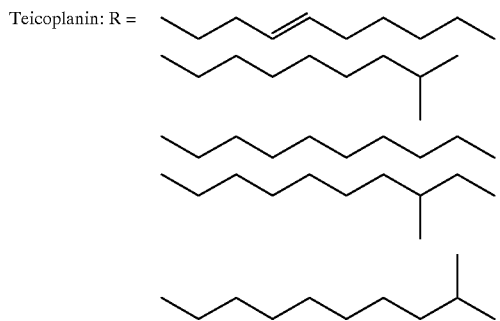

The glycopeptide antibiotics comprise natural and semi-synthetic compounds of highly functionalized linear heptapeptides having a core structure composed of either seven modified or unusual aromatic amino acids, or a mix of aromatic and aliphatic amino acids. Natural glycopeptide compounds have been found in a variety of bacterial genera including Streptomyces, Actinoplanes, Nocardia, Amycolatopsis, Kibdelosporangia, and Pseudonocardia. M. Zmijewski and J. Fayerman. "Glycopeptide Antibiotics," In *Genetics and Biochemistry of Antibiotic Production*, Chap. 18. Ed. L. C. Vining and C. Studtard. Publ. Butterworth Heinemann, Boston (1995). Generally, glycopeptide compounds are differentiated by the placement of sugar substituents on the peptide core. In some instances differentiation arises from the positioning of fatty acid moieties on the sugar substituents. Research has shown that the sugar moieties attached to the core have an effect on the biological activity of glycopeptide molecules.

At present, investigations into glycosylation of glycopeptides and glycopeptide cores are limited to preliminary observations on crude cellular extracts of bacterial strains that produce glycopeptide compounds. These experiments have demonstrated that the glycosylation reaction appears to involve one or more enzymatic activities which attach sugar residues onto a glycopeptide core. One study, for example, demonstrated a glycosylating activity in a crude cellular extract of a vancomycin-producing strain of *Amycolatopsis orientalis*. M. Zmijewski & B. Briggs."Biosynthesis of vancomycin: identification of TDP-glucose:aglycosylvancomycin glucosyltransferase from *Amycolatopsis orientalis*" FEMS Microbiol. Lett. 59, 129–134 (1989).

The glycosylation of glycopeptide compounds, intrinsically interesting from a scientific point of view, presents a number of practical considerations that warrant continued study of this subject. Recently, a number of glycopeptide resistant strains of pathogenic organisms have been encountered within the clinical environment. This trend toward diminished efficacy of glycopeptide compounds is alarming because of a similar phenomenon in the case of β-lactam antibiotics. It is clear that the rise in antibiotic resistance has occurred by a plurality of molecular mechanisms and that resistant organisms possess a diverse repertoire for counteracting the otherwise lethal effect of antibiotic compounds.

In light of the trend toward greater resistance, and in view of the absence of effective alternative treatments, there exists a pressing need to develop new antibiotic compounds. A useful strategy toward this end involves derivitizing presently available glycopeptide compounds by engineering in defined ways the placement and configuration of sugar moieties on the glycopeptide core structure. Achieving molecular rearrangements and substitutions on glycopeptide compounds by chemical means is difficult if not impossible in most cases. By contrast to chemical procedures, enzymatic methods, if available, would provide an effective means to engineer specific modifications onto the glycopeptide core.

The challenge to provide an enzymatic means for modifying glycopeptide core molecules has been met by the present invention. Described herein are gtfA genes isolated from *Amycolatopsis orientalis* that encode glycosyltransferase enzyme GtfA, which adds epivancosamine onto glycopeptides of the vancomycin class.

BRIEF SUMMARY

The present invention is designed to meet the aforementioned need and provides, inter alia, the isolated gtfA gene and other nucleic acid molecules that encode the GtfA gene product from *Amycolatopsis orientalis* A82846. The invention also provides the GtfA protein product of the *Amycolatopsis orientalis* gtfA gene, in substantially purified form.

Having the cloned gtfA gene of *Amycolatopsis orientalis* enables the production of recombinant GtfA protein from which glycopeptide compounds can be made in vitro.

In one embodiment the present invention relates to an isolated DNA molecule encoding GtfA protein, said DNA molecule comprising the nucleotide sequence identified as SEQ ID NO. 1:

```
ATGCGCGTGT  TGATTACGGG  GTGTGGATCG  CGCGGAGATA  CCGAACCGTT  GGTGGCATTG      60

GCGGCACGGT  TGCGGGAACT  CGGTGCGGAC  GCGCGGATGT  GCCTGCCGCC  GGACTACGTG     120

GAGCGGTGCG  CCGAGGTCGG  TGTGCCGATG  GTGCCGGTCG  GTCGGGCGGT  GCGCGCAGGG     180

GCACGCGAGC  CGGGAGAACT  GCCGCCGGGG  GCGGCCGAAG  TCGTGACCGA  GGTGGTCGCC     240

GAATGGTTCG  ACAAGGTCCC  GGCGGCCATC  GAGGGgTGTG  ACGCGGTGGT  GACGACCGGC     300

TTGCTGCCCG  CCGCGGTCGC  TGTCCGGTCG  ATGGCCGAGA  AGCTGGGCAT  CCCGTACCGC     360
```

-continued

```
TACACCGTGC TGTCTCCGGA CCATCTGCCG TCGGAGCAAA GCCAGGCGGA GCGGGACATG       420

TACAACCAGG GCGCCGACAG GCTTTTCGGT GACGCGGTCA ACAGCCACCG GGCCTCGATC       480

GGCCTGCCAC CGGTGGAGCA CCTCTACGAC TACGGCTACA CCGATCAGCC CTGGCTGGCG       540

GCGGACCCGG TGCTGTCCCC GCTGCGGCCG ACGGACCTCG GCACTGTGCA GACCGGTGCG       600

TGGATCCTGC CCGACGAACG GCCGCTTTCC GCGGAGCTGG AGGCGTTTCT GGCTGCCGGG       660

TCGACGCCGG TGTACGTGGG TTTCGGCAGC TCGTCCCGAC CGGCAACCGC TGACGCCGCG       720

AAGATGGCCA TCAAGGCGGT CCGTGCCAGT GGCCGCCGGA TCGTTCTCTC CCGCGGCTGG       780

GCCGATTTGG TCCTGCCGGA CGACGGGGCC GACTGCTTCG TGGTCGGCGA ATGGAACCTT       840

CAGGAGCTGT TCGGCCGGGT GGCCGCCGCC ATCCACCACG ACAGCGCGGG CACGACGCTG       900

CTGGCCATGC GGGCGGGCAT CCCCCAGATC GTGGTGCGCC GCGTAGTGGA CAACGTGGTG       960

GAGCAGGCGT ACCACGCCGA CCGGGTGGCC GAGCTGGGTG TCGGTGTGGC GGTCGACGGT      1020

CCGGTCCCGA CCATCGACTC CTTGTCGGCC GCGCTCGACA CGGCTCTGGC CCCGGAGATC      1080

CGTGCGCGAG TCGACGCGGT CAGCCTGGAA AAGCCGACTG TTCCCGCC                   1188
```

In another embodiment the present invention relates to a glycosyltransferase protein molecule, encoded by SEQ ID NO:1 wherein said glycosyltransferase protein molecule comprises the sequence identified as SEQ ID NO. 2.

In a further embodiment the present invention relates to a ribonucleic acid molecule encoding GtfA protein, said ribonucleic acid molecule comprising the sequence identified as SEQ ID NO. 3:

In yet another embodiment, the present invention relates to a recombinant DNA vector which incorporates the *Amycolatopsis orientalis* gtfA gene in operable linkage to gene expression sequences enabling the gtfA gene to be transcribed and translated in a host cell.

In still another embodiment the present invention relates to homologous or heterologous host cells which have been transformed or transfected with the cloned gtfA gene of *Amycolatopsis orientalis* such that the gtfA gene is expressed in the host cell.

In still another embodiment, the present invention relates to a method for producing glycopeptide compounds wherein recombinantly produced GtfA protein is utilized to add one or more sugar moieties onto a vancomycin glycopeptide in vitro.

In a further embodiment the present invention relates to a composition comprising compound A82846B, said composition produced by the action of recombinant GtfA protein.

DEFINITIONS

"A82846B" refers to a glycopeptide produced by *A. orientalis* A82846 having the structure:

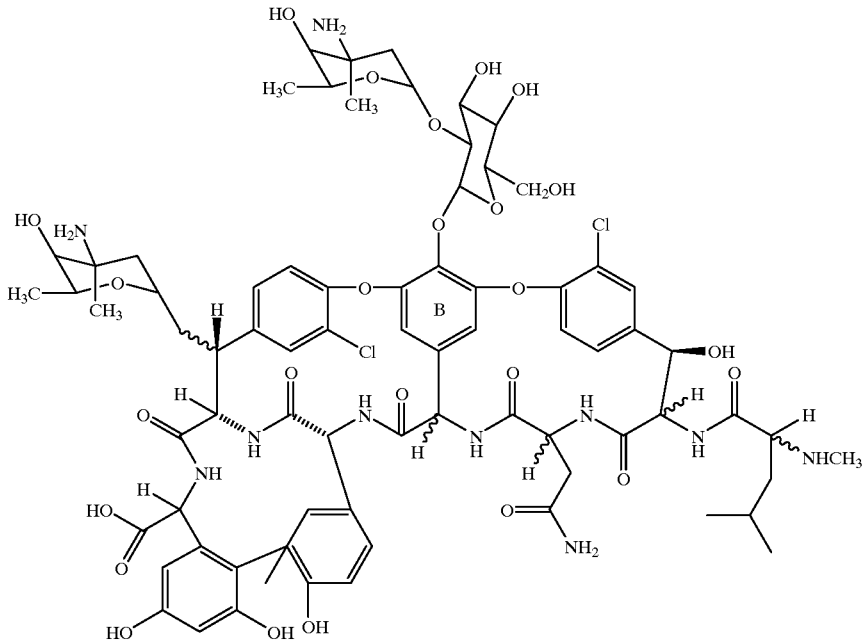

"AGV" denotes aglycosylvancomycin which comprises a vancomycin core having a free hydroxyl group on the B ring in place of the disaccharide moiety.

"DVV" denotes desvancosaminyl vancomycin in which a glucose residue is attached onto AGV at the free hydroxyl position of the B ring.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

The term "glycopeptide" refers to a functionalized linear heptapeptide compound of natural or semi-synthetic origin, said compound having a core structure.

"Glycopeptide core" or "core" or "core compound" interchangeably denote the progenitor structure of all glycopeptide compounds, comprising either 7 modified or unusual aromatic amino acids, or a mix of aromatic and aliphatic amino acids.

"Vancomycin glycopeptide" refers to any or all of the following: AGV, DVV, vancomycin.

"Glycosylating substrate" refers to a compound which functions as a donor of a sugar moiety in an enzymatic glycosylation reaction, for example, uridine diphosphate-D-glucose.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which two or more strands of nucleic acid join through base pairing with complementary strands. "Selective hybridization" refers to hybridization under conditions of high stringency. The degree of hybridization between nucleic acid molecules varies with the degree of complementarity, the stringency of the hybridization conditions, and the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The gtfA gene of *Amycolatopsis orientalis* encodes a glycosylating enzyme, GtfA. The enzyme is involved in glycosylating A82846B and will add epivancosamine onto a vancomycin glycopeptide compound in vitro. The enzyme will use TDP-epivancosamine or UDP-epivancosamine as a glycosylating substrate.

The gtfA gene of *Amycolatopsis orientalis* comprises a DNA sequence of 1188 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product identified as SEQ ID NO:2. All such substitutions are intended to be within the scope of the invention.

Gene Isolation Procedures

Those skilled in the art will recogize that the gtfA gene may be obtained by a plurality of applicable techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the gtfA gene of *Amycolatopsis orientalis* or fragment thereof could also be isolated by PCR amplification of *Amycolatopsis orientalis* genomic DNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990), which hereby is incorporated by reference. The PCR amplification, which comprises genomic DNA, suitable enzymes, primers, and buffers, is conveniently carried out in a DNA THERMAL CYCLER™ (Perkin Elmer Cetus, Norwalk, Conn.). A positive PCR amplification is determined by detecting an appropriately-sized DNA fragment following agarose gel electrophoresis.

Protein Production Methods

One embodiment of the present invention relates to the substantially purified protein GtfA identified as SEQ ID NO:2 and encoded by the gtfA gene or functionally related proteins of *Amycolatopsis orientalis*.

Skilled artisans will recognize that the proteins of the present invention can be synthesized or purified by any number of suitable methods. For example, the amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and are described in a number of general texts on the subject. See, e.g., H. Dugas and C. Penney, *Bioorganic Chemistry* (1981) Springer-Verlag, New York, 54–92. For example, peptides may be synthesized by solid-phase methodology using an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably $-20°$ C. for thirty minutes followed by thirty minutes at $0°$ C.

The proteins of the present invention can also be produced by recombinant DNA methods using the cloned gtfA gene of *Amycolatopsis orientalis*. Recombinant methods are preferred if a high yield is desired. Expression of the cloned gtfA gene can be carried out in a variety of suitable host cells well known to those skilled in the art. The gtfA gene is introduced into a host cell by any suitable transformation, transfection, or conjugation means, well known to those skilled in the art. While chromosomal integration of the cloned gtfA gene is within the scope of the present invention, it is preferred that the gene be cloned into a suitable extra-chromosomally maintained expression vector so that the coding region of the gtfA gene is operably linked to a constitutive or inducible promoter.

The basic steps in the recombinant production of the GtfA protein are:

a) constructing a natural, synthetic or semi-synthetic DNA encoding GtfA protein;

b) integrating said DNA into an expression vector in a manner suitable for expressing the GtfA protein, either alone or as a fusion protein;

c) transforming, transfecting, or otherwise introducing said expression vector into an appropriate eukaryotic or prokaryotic host cell to form a recombinant host cell;

d) culturing said recombinant host cell under conditions that favor expression of the GtfA protein; and e) recovering and purifying the GtfA protein by any suitable means.

Expressing Recombinant GtfA Protein in Procaryotic and Eucaryotic Host Cells

In general, prokaryotes are used for cloning DNA and for constructing the vectors of the present invention. Prokaryotes are also employed in the production of the GtfA protein. For example, the *Escherichia coli* K12 strain 294 (ATCC No. 31446) is particularly useful for the expression of foreign proteins. Other strains of *E. coli*, bacilli such as *Bacillus subtilis*, enterobacteriaceae such as *Salmonella typhimurium* or *Serratia marcescans*, various Pseudomonas species, and other bacteria, such as Streptomyces, may also be employed as host cells in the cloning and expression of the recombinant proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized as the amino acid sequence identified as SEQ ID NO:2, or as a fusion protein comprising the protein of interest and another protein or peptide which may be removable by enzymatic or chemical cleavage. Expression as a fusion protein may prolong the lifespan, increase the yield of the desired peptide, or provide a convenient means for purifying the protein. A variety of peptidases (e.g. enterokinase and thrombin) which cleave a polypeptide at specific sites are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to prokaryotes, mammalian host cells and eukaryotic microbes such as yeast may also be used to isolate and express the genes of the present invention. The simple eucaryote *Saccharomyces cerevisiae*, is the most commonly used eukaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trpl auxotrophic mutant.

Purification of Recombinantly-Produced GtfA Protein

An expression vector carrying the cloned gtfA gene of *Amycolatopsis orientalis* is transformed, transfected, or otherwise introduced into a suitable host cell using standard methods. Cells which contain the vector are propagated under conditions suitable for expression of the Glycosyltransferase protein. If the gtfA gene is under the control of an inducible promoter, growth media and other conditions should incorporate the appropriate inducer.

The recombinantly produced protein may be purified from cellular extracts of transformed cells by any suitable means. In a preferred protein purification method, the gtfA gene is modified at the 5' end to incorporate several histidine residues at the amino terminus of the GtfA protein product. The "histidine tag" enables a single-step protein purification method referred to as "immobilized metal ion affinity chromatography" (IMAC), essentially as described in M. C. Smith et al. "Chelating Peptide-immobilized metal-ion affinity chromatography," Chapter 12, in *Protein Purification: From Molecular Mechanisms to Large Scale Processes*, American Chemical Society, Washington, D.C. (1990), and in U.S. Pat. No. 4,569,794 both of which hereby are incorporated by reference. The IMAC method enables rapid isolation of substantially pure protein.

The gtfA gene, which comprises nucleic acid encoding SEQ ID NO:2, may also be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the gtfA gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. For example, the nucleic acid compounds of the present invention may be used to hybridize to genomic DNA which has been digested with one or more restriction enzymes and separated on an electrophoretic gel. The hybridization of radiolabeled probes onto such restricted DNA, usually fixed to a membrane after electrophoresis, is well known in the art. See, e.g., J. Sambrook, supra. A compound which comprises SEQ ID NO:1, SEQ ID NO:3 or a complementary sequence of SEQ ID NO:1 or SEQ ID NO:3, or a fragment hereof, and which is at least 15 base pairs in length, and which will selectively hybridize to *Amycolatopsis orientalis* DNA or mRNA encoding gtfA, is provided. Preferably, the 15 or more base pair compound is DNA. The probes and primers of this invention can be prepared by techniques well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1.

Choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers and metabolic markers), and the desired number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. A number of inducible promoters responding to a variety of induction signals are available, for example, carbon source, metal ions, and heat. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. A preferred host cell is any strain of *E. coli* which can accomodate high level expression of a gene(s) introduced by transformation or transfection. Preferred vectors for expression are those which comprise SEQ ID NO:1. A preferred expression vector for use in *E. coli* is plasmid pCZA364, which comprises SEQ ID NO:1. (See Example 1). Transformed host cells may be cultured under conditions well known to skilled artisans such that SEQ ID NO:2 is expressed, thereby producing GtfA protein in the recombinant host cell.

The cloned GtfA enzyme is useful for glycosylating vancomycin glycopeptide compounds. A method embodied herein comprises glycosylating a vancomycin glycopeptide compound, by contacting the glycopeptide with the cloned GtfA protein in the presence of a suitable substrate, and monitoring the glycopeptide compound that is produced.

The instant invention provides an enzymatic method for glycosylating glycopeptides of the vancomycin class using the cloned *A. orientalis* gtfA gene, said method comprising the steps of:

a) expressing the cloned gtfA gene in a host cell so that GtfA enzyme is produced;

b) exposing said GtfA enzyme to a glycopeptide compound, in vitro;

c) introducing a suitable glycosylating substrate; and d) characterizing and/or purifying the product glycopeptide by any suitable means.

The instant method can be used to enzymatically attach epivancosamine to glycopeptide molecules of the vancomycin class.

The method can be implemented using substantially purified recombinant GtfA protein, as described herein, or using a crude cellular extract isolated from a recombinant cell culture that expresses the GtfA protein by virtue of having been transformed or transfected with the gtfA gene.

A suitable substrate for the in vitro glycosylation reaction comprises TDP-epivancosamine. This substrate can be obtained by acid-catalyzed hydrolysis of compound A82846B using any suitable method known to skilled artisans (See e.g. M. Sim et al. "Synthesis and use of glycosyl phosphites: an effective route to glycosyl phophates, sugar nucleotides, and glycosides" J. Am. Chem. Soc. 115, 2260–67 (1993)). In one method for preparation of this substrate, following acid hydrolysis of A82846B the hydrolytic products are condensed with dibenzyl N,N-diethylphosphoramidite as a phosphitylating reagent so as to generate the appropriate dibenzyl glycosyl phosphite derivative. Oxidation and deprotection, followed by reaction with thymidine 5'-monophospho-morpholidate provides the desired sugar substrate.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing Amycolatopsis orientalis Gene gtfA in Escherichia coli Plasmid pCZA364 is an approximately 7 kilobasepair expression vector suitable for expressing the gtfA gene at high levels in a procaryotic host, for example E. coli. The backbone of plasmid pCZA364 is derived from parent plasmid PET-11a (obtained from Novagen, Madison, Wis.), which contains an origin of DNA replication (ori), an ampicillin resistance gene (Amp), the T7 promoter region, and the lacI gene for repressing the lac operon.

The gtfA gene cassette inserted into pCZA364 is generated using the PCR carried out on A. orientalis A82846 genomic DNA using standard conditions. Primers used in the amplification reaction are complementary to the 5' and 3' ends of the gtfA gene sequence specified in SEQ ID NO: 1 and are engineered to contain NdeI and BglII restriction sites. The PCR-amplified gtfA gene sequence is digested with NdeI and BglII and ligated into pET11a, which has been digested with NdeI and BamHI.

EXAMPLE 2

Transformation of Escherichia coli with an Expression Plasmid Carrying the gtfA Gene of Amycolatopsis orientalis Plasmid pCZA364 is transformed into E. coli BL21(DE3) (hsdS gal λcIts857 ind1Sam7nin5lacUV5-T7gene 1) using standard methods (See e.g. Sambrook et al. Supra).

EXAMPLE 3

In Vitro Glycosylation of Aglycosylvancomycin Using Cloned gtfA Gene

Approximately 25 ml of a culture of E. coli BL21(DE3) cells transformed with plasmid pCZA364 is grown to an $OD_{600}$ of about 0.6. Induction of gtfA gene expression is effected by adding 1 mM isopropyl-β-D-thiogalactoside (IPTG) with shaking at room temperature for 2 to 3 hours. Thereafter, cells from about 20 ml of the induced culture are pelleted by centrifugation and resuspended in 2 ml of 50 mM Tris pH 9.0, 100 μg/ml lysozyme with incubation on ice for 10 minutes to effect cell lysis. After cell lysis the suspension is passed through a 23-gauge syringe and centrifuged at 10,000×g for 15 minutes to pellet cell debris. The resulting cell extract is used to attach epivancosamine onto AGV. The 1 ml glycosylation reaction contains:

1 mg AGV in 50 mM Tris HCL, pH 9.0
5 mg TDP-epivancosamine
1 mg bovine serum albumin (BSA)
20 μl 1 M MgCl2
20 μl 1 M CaCl2
5 μl 1 M dithiothreitol (DTT)
445 μl cell extract
Distilled water to 1 ml.

A control reaction contains cell extract from non-transformed BL21(DE3). After incubation overnight at 37° C. with slight shaking the reaction is filtered through a 0.45 micron filter and analyzed by HPLC.

We claim:
1. A substantially pure glycosyltransferase protein from *Amycolatopsis orientalis* having the amino acid sequence.

* * * * *